United States Patent [19]
Schmitz et al.

[11] Patent Number: 5,610,712
[45] Date of Patent: Mar. 11, 1997

[54] LASER DIFFRACTION PARTICLE SIZING METHOD USING A MONOMODE OPTICAL FIBER

[75] Inventors: Brian D. Schmitz, Pompano Beach; Steven E. Bott, Pembroke Pines; William H. Hart, Miami, all of Fla.

[73] Assignee: Coulter Corporation, Miami, Fla.

[21] Appl. No.: 545,424

[22] Filed: Oct. 9, 1995

Related U.S. Application Data

[63] Continuation of Ser. No. 73,143, Jun. 4, 1993, abandoned.
[51] Int. Cl.$^6$ .................... G01N 15/02; G01N 21/47
[52] U.S. Cl. .................... 356/335; 356/336; 356/338; 356/343
[58] Field of Search .................... 356/336, 338, 356/343, 339, 367, 73, 39; 359/558, 559, 335

[56] References Cited

U.S. PATENT DOCUMENTS

| | | | |
|---|---|---|---|
| 4,975,237 | 12/1990 | Brown | 356/338 |
| 5,498,904 | 1/1996 | Horn et al. | 356/73 |

*Primary Examiner*—Jon W. Henry
*Attorney, Agent, or Firm*—John T. Winburn

[57] ABSTRACT

A fiber optic spatial filter assembly for laser diffraction particle sizing apparatus utilizing a laser to generate a monochromatic light beam which is coupled to an optical fiber operating substantially in a monomode and creating a beam of light having a high degree of spatial coherence which is then passed through collimating lenses to interrogate and impinge upon the particles of matter through which the laser diffracted light passes. The light scattered by the particles is focused onto a Fourier plane and thereafter impinges upon a photooptical detector array, positioned coincident with the Fourier plane, for measuring the light intensities of the scattered light by scattering angle, thus enabling the computation of particle size.

5 Claims, 4 Drawing Sheets

LASER DIFFRACTION PARTICLE SIZING METHOD USING A MONOMODE OPTICAL FIBER

This application is a continuation of application Ser. No. 08/073,143, filed Jun. 4, 1993 now abandoned.

BACKGROUND OF THE INVENTION

1. Field of the Invention

The present invention generally relates to apparatus and method for particle sizing of the type which employs laser diffraction to measure particle size. The present invention, more specifically, uses, with other components, a monomode optical fiber for producing a beam of light having a high degree of spatial coherence in a spatial filter that is easily aligned, replaceable, rugged and cost effective.

2. Description of Prior Art

The use of laser light diffraction to measure particle size is a widely known technique. Laser diffraction is a particle sizing method which uses the average relative angular intensity of scattered light. Instruments that use laser light diffraction to measure particle size have been available for many years from a number of different manufacturers. All laser diffraction instruments use the same basic method to measure particle size. All laser diffraction instruments require a beam of monochromatic light with a very uniform wave front. This beam of laser light is directed at the sample particles to be measured. When the light hits the particles, the light is diffracted or scattered from the particles. Detectors are used to measure the relative average intensity of the light scattered at various angles from the sample material. Once the relative intensity of light scattered at several different angles from the particles is known, the particle size and size distribution can be calculated.

The ability to make accurate measurements of particle size is directly related to the quality of the beam, its spatial coherence, which illuminates the sample particles. This monochromatic light beam must be highly collimated, meaning that all the rays of light traveling in the beam are parallel to one another.

In order for a beam of light to be highly collimated, the light must have a very uniform wave front from the light source. Ideally the light source would be a perfect point source of light, infinitesimally small. Also, the light source must be free of diffraction, which could be caused by dust particles in the air, or because the light beam is partially obstructed. In addition, any optical lenses used to collimate the beam of light must be free of surface and material imperfections which would also cause light diffraction. Finally, any optical lenses use to collimate the beam must be designed to minimize any aberrations caused by the lens itself. These characteristics are necessary to achieve high resolution size measurements.

Apparatus and method using laser diffraction to measure particles is importantly different from dynamic light scatter apparatus and method for particle analysis. Dynamic light scatter requires time fluctuation, or power spectral measurement of the scattered light. Whereas, laser diffraction requires measurement of average, relative angular intensity of the scattered light at a number of detection angles, which is not a time or frequency based measurement. The basic differences between structures, methods, and optical requirements of laser diffraction versus dynamic light scatter are known to those in these fields. However, some sophisticated and subtle differences of laser diffraction might not be appreciated by those knowledgeable in dynamic light scatter technology.

In laser diffraction devices, such as the COULTER® LS and competitive devices, spatial filtering of the laser beam is used to create the above discussed high spatial coherence quality beam and is one of the most important aspects of the instrument. In the COULTER LS, in order to measure the small angular deflection of the laser beam caused by diffraction from very large particles such as nine hundred micrometers (900 µm), light scattered at angles as small as 0.5 milliradians (mR) must be measured and an angular resolution of approximately 0.05 mR is desired. To achieve this level of beam quality, the laser beam must be expanded to about thirteen millimeters (13 mm) and a diffraction limited beam of this diameter must be formed by the collimating optics. A diffraction limited Gaussian beam of thirteen (13) mm diameter, with a wavelength of seven hundred and fifty nanometers (750 nm), has a divergence of ~0.04 mR. Any serious discrepancy between this desired level of spatial coherence and collimation and the actual performance leads to degradation in the resolution of the instrument.

All particle sizing instruments based on laser diffraction techniques use a spatial filter to provide this very high quality beam of laser light. All of these spatial filters use a pinhole in combination with other optical elements to create the required quality light beam. A pinhole is a small, circular hole in a thin, flat piece of rigid, opaque material. A typical pinhole spatial filter is configured in the following manner. A source of light, such as a laser diode, illuminates a circular beam stop, which makes the light beam circular. The circular light beam then passes through a system of optical lenses. These lenses focus the laser beam down to the pinhole, which is typically between twenty to fifty (20–50) µm in diameter, allowing most of the light beam to pass through the pinhole. Any impurities in the laser light, caused by diffraction or lens aberration do not pass through the pinhole, but are blocked by the opaque material surrounding the pinhole. The light that passes through the pinhole is then "clean," except for some diffraction rings caused by the pinhole itself. These diffraction rings are removed by another beam stop placed at the exact minimum of the first diffraction ring. Finally, a lens collimates this diverging, circular beam of light at the point the desired beam diameter, thirteen (13) mm in the case of the COULTER LS, is reached, creating a highly collimated, uniform wave front beam of light, which is useful for laser diffraction particle sizing.

While the pinhole method of creating this beam of light works effectively, in practice it has many problems. First, in order to pass most of the light from the laser source through the pinhole, the optical elements including the source, the first beam stop, the lenses and the pinhole, must be precisely focused and aligned to within a few micrometers. This requires the use of very complicated and expensive mechanical elements to provide the fine resolution these adjustments require. Additionally, the time required to sufficiently adjust the assembly can be many hours. Secondly, once the assembly is fully aligned, it can be easily misaligned by mechanical distortions from clamping, or from temperature changes, which cause the various components to expand per their respective coefficients of thermal expansion. Also, shock and vibration during shipment of the instrument can cause the pinhole assembly to become misaligned, causing expensive, time consuming field service. Once in use in the laboratory, if a component of the spatial filter optical train burns out or is damaged, the entire optical assembly must be returned to the factory for parts replacement and then the time consuming, expensive optical realignment.

Thus, it would be advantageous for laser diffraction particle analysis apparatus to improve upon the pinhole style of spatial filter assembly to reduce or eliminate the above mentioned drawbacks. Alternatively, if the pinhole and other associated components could be replaced to provide an assembly that is much more rugged, much more immune to distortions caused by thermal effects, shock and vibration, requires very little alignment, and is lower cost, such replacement would solve a longstanding need.

Many devices, for example those described in one or more of the hereinafter listed publications, utilize various forms of optical fibers, including monomode and multimode fibers, in light transmitting and light detecting arrangements. However, none of the prior art devices describe a monomode optical fiber apparatus in a spatial filter capable of providing the high quality light beam required for particle sizing using laser diffraction techniques.

U.S. Pat. No. 4,953,978, Steven E. Bott et al., Coulter Electronics of New England, Inc., PARTICLE SIZE ANALYSIS UTILIZING POLARIZATION INTENSITY DIFFERENTIAL SCATTERING.

U.S. Pat. No. 4,975,237, Robert G. W. Brown, The Secretary of State for Defence in Her Britannic Majesty's Government of the United Kingdom of Great Britain and Northern Ireland, DYNAMIC LIGHT SCATTERING APPARATUS.

U.S. Pat. No. 5,056,918, Steven E. Bott et al., Coulter Electronics of New England, Inc., METHOD AND APPARATUS FOR PARTICLE SIZE ANALYSIS.

Juskaitis, R., et al., 1992, *Electronics Letters* Vol. 28(11), FIBRE-OPTIC BASED CONFOCAL SCANNING MICROSCOPY WITH SEMICONDUCTOR LASER EXCITATION AND DETECTION.

Brown, R. G. W., et al., 1987, *J. Physics E, Vol.* 20, MONOMODE FIBRE COMPONENTS FOR DYNAMIC LIGHT SCATTERING.

Brown, R. G. W., 1988, HMSO, MINIATURE INSTRUMENTATION FOR LASER LIGHT SCATTERING EXPERIMENTS.

Knuhtsen, J., et al., 1982, *The Institute of Physics*, FIBRE-OPTIC LASER DOPPLER ANEMOMETER WITH BRAGG FREQUENCY SHIFT UTILISING POLARISATION-PRESERVING SINGLE-MODE FIBRE.

Brown, R. G. W., 1987, *Applied Optics*, Vol. 26(22), DYNAMIC LIGHT SCATTERING USING MONOMODE OPTICAL FIBERS.

Dabbs, T., et al., 1992, *Applied Optics*, Vol. 31(16), FIBER-OPTIC CONFOCAL MICROSCOPE: FOCON.

Brown, R. G. W., 1987, DESIGNS OF FIBRE OPTIC PROBES FOR LASER ANEMOMETRY: Paper 9, *Second International Conference on Laser Anemometry— Advances and Applications*, Strathclyde, UK.

U.S. Pat. No. 4,975,237 to Brown relates to the use of monomode optical fibers in a light detector assembly, in a dynamic light scatter apparatus. Brown describes the substitution of a pinhole in front of a photo detector with a monomode optical fiber, the purpose of which is to isolate a small area of light from a large amount of scattered light from the particles. Brown uses a monomode optical fiber simply because the core diameter of the monomode fiber is of approximately the correct size to isolate a single coherence area of scattered light. Brown does not use an optical fiber as a light delivery and filtering device suitable for laser diffraction. In FIG. 1 of Brown, a monomode optical fiber is shown in a beam delivery path. Brown does not, however, teach or suggest benefits of spatial filtering employing the monomode optical fiber, because the Dynamic Light Scattering method of his device does not require the beam quality required of the laser diffraction sizing apparatus.

Other apparatus, such as the confocal microscope of Juskaitis et al., use monomode optical fibers for both delivery and detection of light. Such devices and their methods are not related to laser diffraction particle sizing and do not teach the use of monomode optical fibers in spatial filter assemblies for such.

SUMMARY OF THE INVENTION

It has been discovered and demonstrated that a monomode optical fiber can be used in a spatial filter assembly to provide the filtering benefits of conventional, pinhole-based spatial filter assemblies, for producing the spatially clean, uniform wave front, point source of monochromatic light that is required for laser diffraction techniques of particle sizing. The obtained point source of light is closer to the ideal point source. The spatial coherence is especially of high degree. The optical fiber-based filtering assembly provides the additional benefits of being less expensive, more rugged, easier to align and more resistant to thermal and vibration effects.

DETAILED DESCRIPTION OF A PREFERRED EMBODIMENT OF THE PRESENT INVENTION

Figure 1:
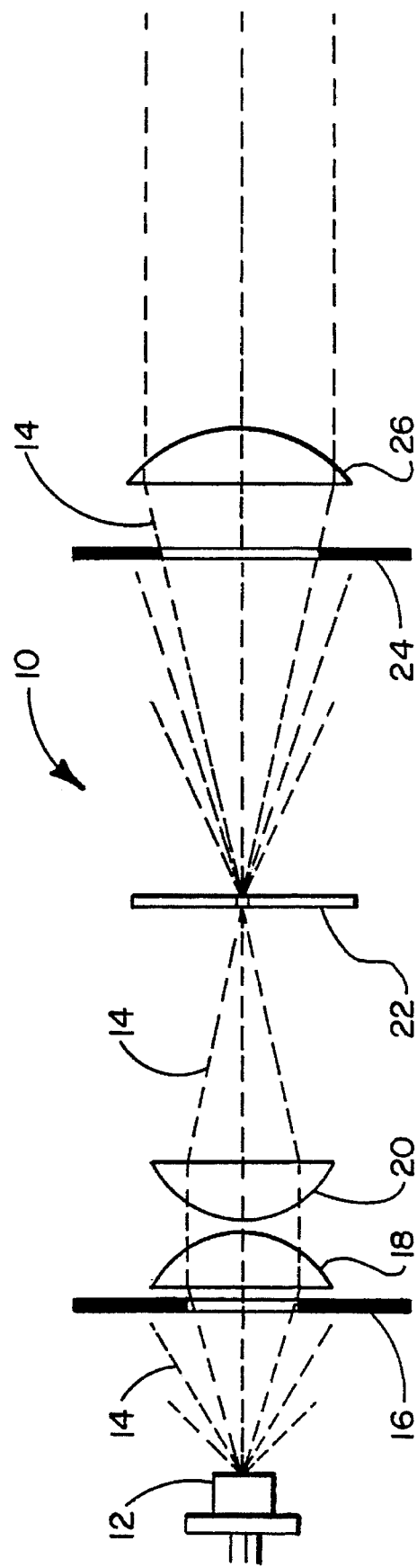
FIG. 1, is a diagrammatic representation of a typical, conventional, prior art pinhole spatial filter.

As illustrated in the diagrammatic view of FIG. 1 of the drawing, a conventional, prior art pinhole-based spatial filter 10, generally includes: a light generating laser diode 12, the beam 14 of which is passed to a first circular beam stop 16, which acts to eliminate unwanted peripheral light rays and makes the light beam circular in shape; focusing lenses 18 and 20; a pinhole member 22; a second beam stop 24 to remove diffraction rings caused by parts of the beam 14 hitting the edges of the pinhole 22; and finally, the laser light beam is collimated by a lens 26 and passed on into a sample containing cell, passageway or flow path (not shown) for sizing particulate matter contained therein. The second beam stop 24 and the collimating lens 26 are required parts of the prior art spatial filter arrangement. Imperfections in the lenses 18 and 20 and dust particles between the laser source and the pinhole can cause some diffraction of the beam 14 and form unwanted or "dirty" light rays which do not pass through the pinhole 22, but are blocked.

Figure 2:
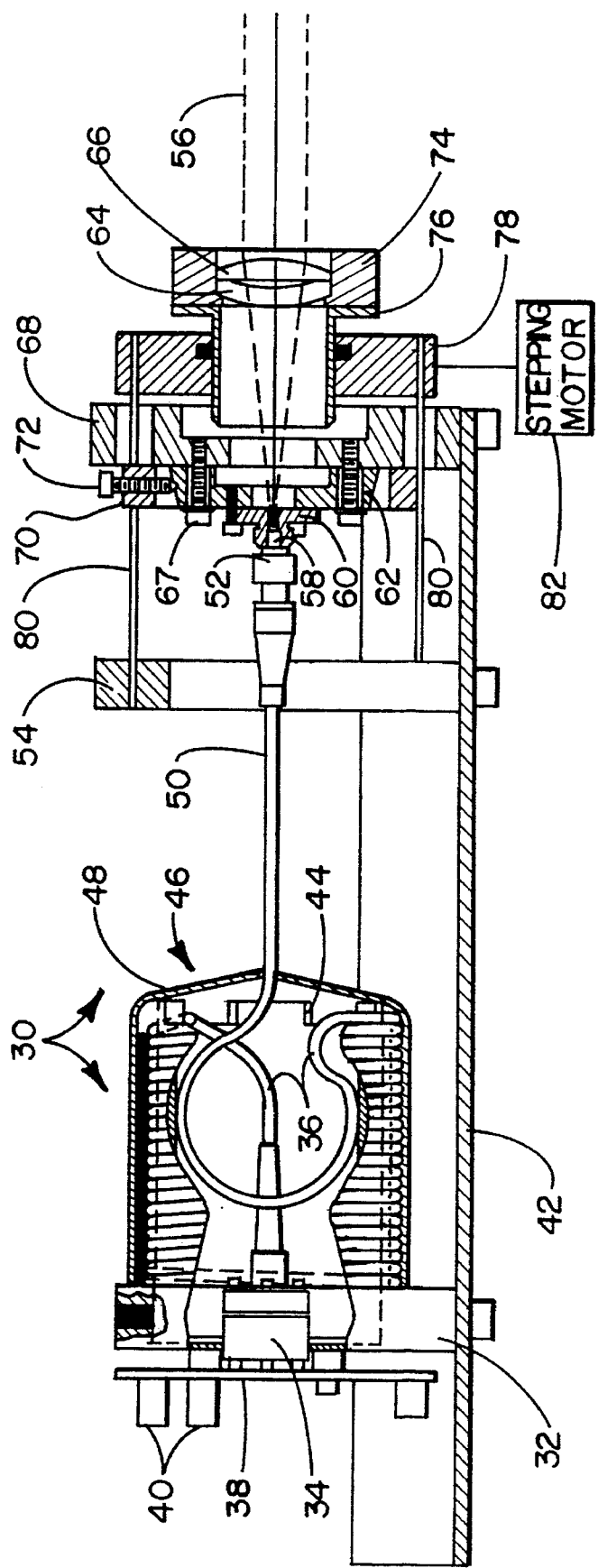
FIG. 2, is a side elevation, partial sectional view of an optical fiber-based spatial filter embodying the present invention.

In contrast to the foregoing prior art, the optical fiber-based spatial filter of the laser diffraction particle sizing apparatus embodying the present invention is illustrated in FIG. 2 of the drawings, and will be described presently.

Figure 3:
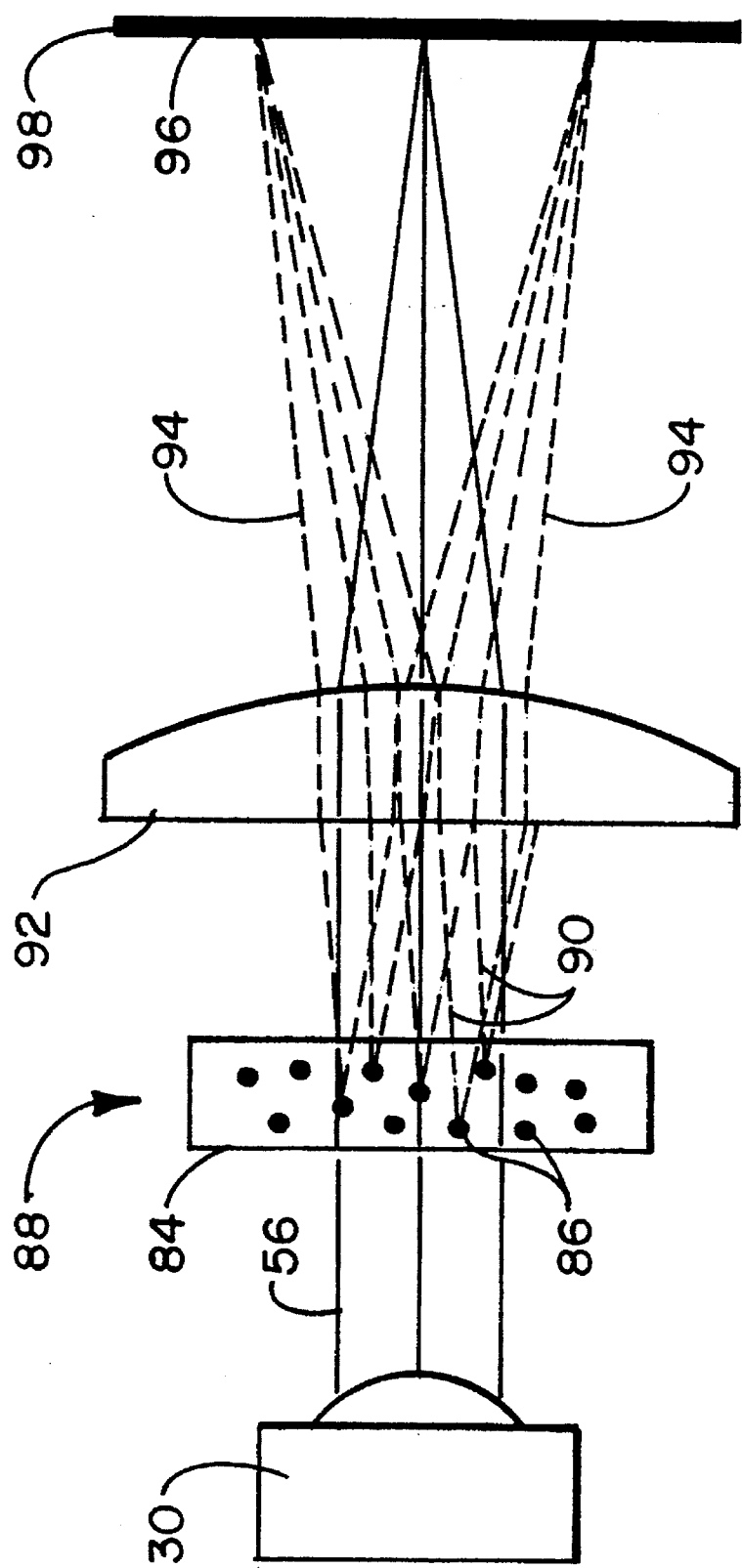
FIG. 3, is a diagrammatic representation of a laser diffraction apparatus utilizing the optical fiber-based spatial filter assembly embodying the invention.
Figure 4:
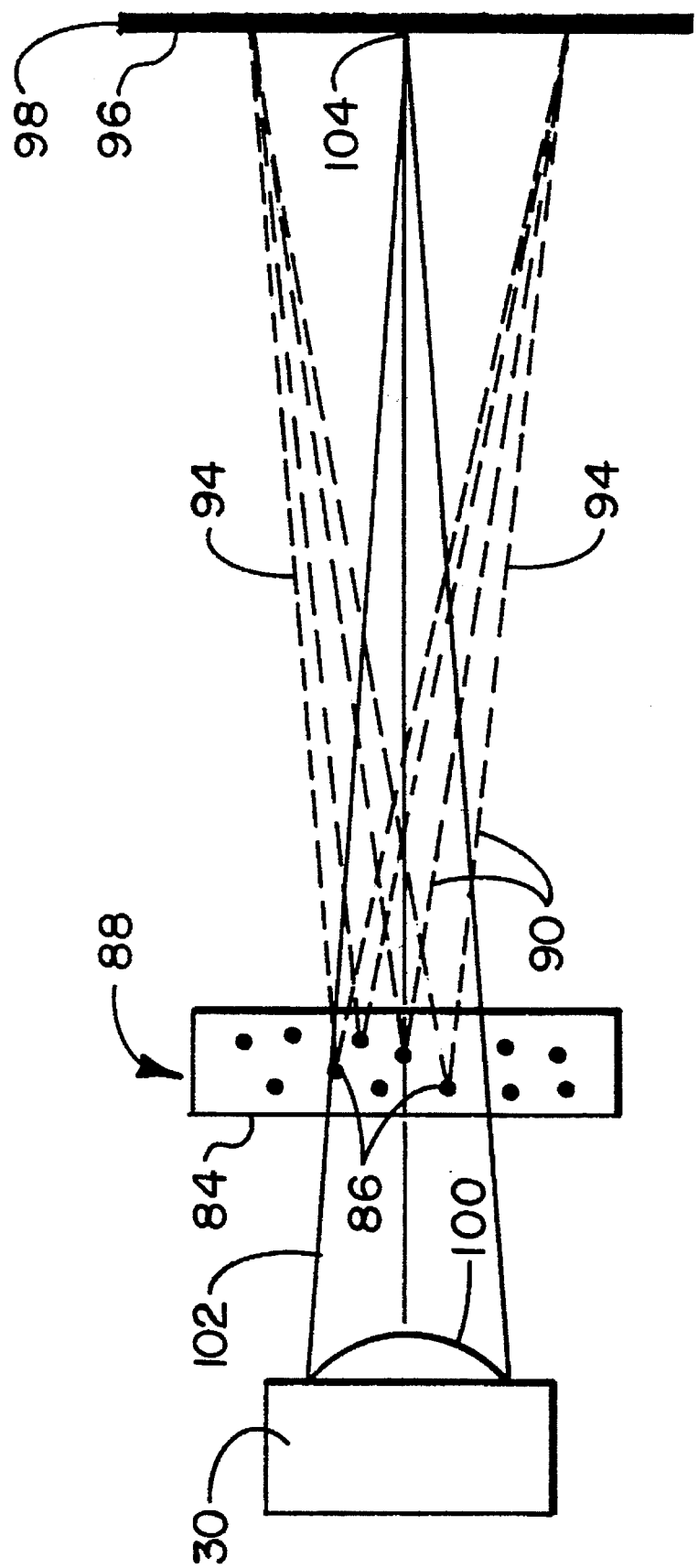
FIG. 4 is a diagrammatic representation, similar to FIG. 3, using a reverse Fourier lens.

Laser diffraction particle sizing apparatus incorporating the novel optical fiber-based spatial filter assembly of this invention are illustrated in FIGS. 3 and 4 of the drawings.

As shown in FIG. 2, a monomode optical fiber-based spatial filter assembly 30 according to the preferred embodiment includes many elements. A first rigid, vertical support member 32 supports a laser diode to optical fiber coupler 34, which couples the light from a laser diode (35) into a monomode optical fiber cable 36. The construction of optical fiber couplers are widely available, as used in the telecommunications industry. The optical fiber cable 36 is cut to approximately six meters in length. The specific length is not critical to the invention, but must be sufficiently long so that the extraneous light traveling through the cladding (not shown) of the fiber is attenuated to the extent that it is not detrimental to the output of a clean, spatially filtered beam. The fiber optic coupler 34 is supported by a printed circuit board 38, which provides a mounting member for individual circuit components 40, not otherwise described, which apply electrical power to the laser diode (not shown). The printed circuit board 38 is supported by the first rigid support member 32 which itself is disposed on a rigid base member 42. The support member 32 also supports a short cylindrical form or tube 44. The six meter length of the optical fiber cable 36 is wrapped in a coil around the cylindrical tube 44, to provide a relatively small, compact assembly 46, which is thereafter covered by a shrink-wrap cover 48, which protects the cable from damage due to handling. A forwardly extending end 50 of the optical fiber cable 36 is terminated with an optical fiber connector 52, to permit the assembly 46 to be replaced in the field, if parts thereof are damaged or burn out.

The optical fiber 36 is a monomode (single mode) optical fiber with a core diameter of approximately five (5) μm and a cladding diameter of one hundred and twenty-five (125) μm. An optical fiber is defined as being single mode for a given wavelength of light when the Normalized Frequency (V-number) of the fiber is less than or equal to 2.405. The V-number is calculated as follows:

$$V = \frac{2\pi(NA)a}{\lambda}$$

where:

NA=numerical aperture of the fiber (dimensionless)

a=fiber core radius (μm)

λ=light wavelength (μm)

In an embodiment of the present invention, the numerical aperture of the optical fiber was 0.11, the wavelength of the laser light 750 nm and the fiber core radius 2.5 μm. This design yields a V-number of 2.30.

Fiber couplers, such as the coupler 34, typically have means to secure the laser diode in place relative to a lens which focuses the light onto the input face of the optical fiber. Fiber couplers can be purchased with different degrees of coupling efficiency, but generally less than 45%; meaning that only 45% of the output power of the laser diode is coupled into the optical fiber. However, this coupling efficiency is one to three times better than the efficiency found in a typical pinhole-based filtering assembly. In the preferred embodiment of the present invention, a laser diode with five milliwatt (5 mW) output power is coupled into the optical fiber 36 with approximately 20% efficiency, for producing output power of the fiber of approximately one (1) mW.

Most of the light that is coupled into the optical fiber travels through the core of the optical fiber, but a portion of the light is coupled into the cladding of the optical fiber. This "cladding light" can be a source of very poor performance of the spatial filter if it is not adequately extinguished. In the embodiment of the present invention, a relatively long length of optical fiber is used, approximately six meters, to allow the light traveling through the cladding to be extinguished due to the inherently high attenuation losses of the cladding. Alternatively, this cladding mode light could be removed from the cladding through the use of an index matching gel surrounding the cladding along the fiber.

After the cladding light traveling through the fiber has been sufficiently attenuated, the light leaves the end of the fiber through its core (5 μm diameter). This core diameter used with seven hundred and fifty (750) nm light caused the light output of the monomode optical fiber to be closer to an ideal point source of light than the typical pinhole spatial filter, which uses a pinhole of twenty to fifty (20–50) μm diameter. Also, due to the core diameter and limited numerical aperture of the light output from a monomode optical fiber, there is no need for the second beam stop 24 required in the typical prior art pinhole type filter of FIG. 1.

The optical fiber connector 52 is mounted through a second, rigid, vertical support member 54, which also is secured to the base member 42. The laser light beam 56 exits the end or tip 58 of the optical fiber 36. Due to the nature of the monomode optical fiber, the light exiting the optical fiber has wave front distortion typically less than λ/10, is circular in shape, has a Gaussian intensity profile, and diverges according to the numerical aperture of the fiber, which in the preferred embodiment was 0.11. In the preferred embodiment, the output beam 56 has a high degree of spatial coherence and is allowed to expand to approximately thirteen (13) mm in diameter before being collimated.

The optical fiber connector 52 attaches to a female connector member 60, which in turn is attached to a rigid positioning disk 62. During assembly, the disk 62 allows the tip 58 of the optical fiber 36 to be statically centered to the nominal center position of a pair of collimating or beam forming lenses 64 and 66. The positioning disk 62, by way of locking screws 67, is held in place on a second vertical support member 68, which also is mounted to the base member 42.

The positioning disk 62 is located inside of a positioning ring 70, which provides mounting for two adjustment screws 72 (only one of which is shown). The adjustment screws 72 move the positioning disk 62 and thereby the fiber tip 58 in both an X and Y axis direction, allowing the beam of light 56 to be centered at the nominal center of the beam forming lenses 64 and 66. Once the positioning disk 62 is centered, the locking screws 67 are tightened, securing the position of the disk 62 to the vertical support member 68 and the base member 42.

The lenses 64 and 66 are disposed in a lens mount 74, which is secured to a lens tube 76, which is slidable along the Z axis through a block-like support member 78, such sliding permitting the lenses to be focused. Once focusing is accomplished, a set screw (not shown) retains the lens tube 76 in place with respect to the support block member 78.

The lenses 64 and 66 are positioned relative to the X and Y axes by moving the block 78. This block 78 is flexibly supported from the support member 54 by four equidistant, corner disposed, flexible wire-like members 80 extending from the first support member 54 forwardly through clearance holes in the second vertical support member 68 to the block 78. Through the use of two stepper motors 82 (only one shown), the block 78 is positioned in an X-Y orientation and combinations thereof. This flexible construction allows the laser diffraction apparatus to dynamically align the light beam 56 with respect to the rest of the apparatus.

As seen in the diagrammatic view of FIG. 3, the laser diffraction particle sizing apparatus embodying the present single mode optical fiber-based filter assembly 30 is illustrated with the collimated laser light beam 56 passing into and through a sample passageway 84, through which particulate matter 86 of varying size particles moves or flows in the direction of the arrow 88. The passageway 84 can be a flow cell, a sample stream flowing in air, or a stream of sample sheathed by another media. It is not essential for the particle sample to be flowing. The particles 86 (shown in this figure to be the same size for simplification) diffract some of the impinging laser light beam in accordance with the well-known Fraunhofer diffraction and other scattering theory. The light diffracted from the beam becomes a plurality of diffracted rays 90 of light spreading away from the particles, as illustrated in FIG. 3. The angle of the diffracted light 90 relative to the collimated light beam 56 is roughly inversely proportional to the size of the particles 86.

The diffracted light 90 then passes through a Fourier lens 92, which causes light of a given angle 94, incident on the lens, to be focused onto a Fourier surface or plane 96, which is displaced from the Fourier lens 92 by a distance equal to the focal length of that lens. A photo detector 98 is positioned coincident with the Fourier plane 96. The photo detector array 98 is made up a large number of individual photo detectors which measure light intensity. By measuring the light intensity at a large number of detector locations on the photo detector array 98, a precise profile of scattered light intensity versus scattering angle is obtained. A computer (not shown) operably associated with the laser diffraction sizing apparatus can determine the actual size and size distribution of the sample particles 86.

FIG. 4 illustrates an embodiment of the invention in which the collimating lens 64 and 66 are replaced by a reverse Fourier lens 100, itself well known in the art. The reverse Fourier lens 100 obviates the need for the Fourier lens 92 of FIG. 3, but has as its Fourier plane the same plane 96 as the Fourier lens 92 in FIG. 3. The reverse Fourier lens 100 produces a convergent beam 102, which converges at a point 104 on the Fourier plane; the convergence point 104 also being the same for the Fourier lens 92. The reverse Fourier lens 100 and the collimating lenses 64 and 66 are generically identified as "beam forming means".

In summary, the present invention provides the same functions as the conventional pinhole-based spatial filter assemblies, but without its second beam stop, expensive alignment assemblies, the high cost associated with the time-consuming alignment procedure and the expensive field service problems associated with shipping the delicate pinhole-based filter. The laser light output beam of the monomode optical fiber-based filter is of better quality, spatial coherence, than the typical pinhole-based filter because the size of the effective light emitting source is closer to the ideal point source of light. For example, with optical fiber-based technology, a five μm core diameter can be achieved quite readily; whereas, a pinhole-based filter of equivalent size would be practically impossible to align and successfully ship in a commercial product.

It is understood that the illustrative embodiments constitute examples of the principles of the present invention, but that alternatives will occur to those of ordinary skill in the art, without departure from the scope of this invention.

What we claim is:

1. A method for determining the respective sizes and size distribution of a plurality of particles disposed in a sample containing said particles, said method comprising the steps of:

a) providing a laser beam;

b) passing said laser beam through a monomode optical fiber to produce, at one end of said fiber, a point source of light having a high degree of spatial coherence;

c) focusing light emanating from said point source to produce a collimated, diffraction-limited beam of light having a high degree of spatial coherence and a diameter substantially greater than the size of any of said particles;

d) illuminating said particle-containing sample with said diffraction-limited beam thereby producing a plurality of diffracted beams at different diffraction angles relative to the direction of said diffraction-limited beam;

e) focusing the diffracted beams with a lens at the Fourier plane of said lens;

f) simultaneously measuring the intensity of the diffracted beams at different locations in said Fourier plane with a plurality of detectors; and g) determining the size and particle distribution based on the respective outputs of said detectors.

2. The method as defined by claim 1 wherein said diffraction-limited beam has a diameter of greater than 1 mm.

3. The method as defined by claim 1 wherein said diffraction-limited beam has a diameter of about 10 mm.

4. The method as defined by claim 1 wherein said optical fiber comprises a cladding layer surrounding a central arc, and wherein said fiber has a length sufficient to effectively eliminate unwanted propagation of laser light in said cladding layer.

5. The method as defined by claim 4 wherein said optical fiber has a length of about six feet.

\* \* \* \* \*